United States Patent
D'Ambrogio et al.

(10) Patent No.: US 9,480,631 B2
(45) Date of Patent: Nov. 1, 2016

(54) SHELF STABLE CAPSULES

(75) Inventors: Robert D'Ambrogio, Princeton, NJ (US); Shira Pilch, Highland Park, NJ (US); James Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 114 days.

(21) Appl. No.: 13/128,243

(22) PCT Filed: Nov. 10, 2008

(86) PCT No.: PCT/US2008/082954
§ 371 (c)(1),
(2), (4) Date: May 9, 2011

(87) PCT Pub. No.: WO2010/053492
PCT Pub. Date: May 14, 2010

(65) Prior Publication Data
US 2011/0223226 A1    Sep. 15, 2011

(51) Int. Cl.
| A61K 8/11 | (2006.01) |
| A61K 47/10 | (2006.01) |
| A61K 47/18 | (2006.01) |
| A61K 9/48 | (2006.01) |
| G01N 33/98 | (2006.01) |
| A61K 8/34 | (2006.01) |
| A61Q 11/00 | (2006.01) |

(52) U.S. Cl.
CPC ............ *A61K 8/11* (2013.01); *A61K 8/345* (2013.01); *A61Q 11/00* (2013.01)

(58) Field of Classification Search
CPC ......... A61K 8/11; A61K 8/345; A61Q 11/00
USPC ................... 424/401, 452, 49; 514/772, 784
See application file for complete search history.

(56) References Cited

U.S. PATENT DOCUMENTS

| 4,002,718 A | 1/1977 | Gardella et al. |
| 4,071,614 A | 1/1978 | Grimm |
| 4,459,277 A * | 7/1984 | Kosti ............................ 424/9.71 |
| 5,300,305 A | 4/1994 | Stapler et al. |
| 5,700,449 A | 12/1997 | Katayama et al. |
| 6,045,835 A | 4/2000 | Soper et al. |
| 6,193,999 B1 | 2/2001 | Gennadios |
| 6,287,542 B1 * | 9/2001 | Bernard et al. .................. 424/49 |
| 6,730,651 B2 | 5/2004 | Hsu et al. |
| 2003/0044359 A1 | 3/2003 | Wuelknitz et al. |
| 2005/0084460 A1 * | 4/2005 | Winston et al. ................ 424/49 |
| 2006/0153909 A1 | 7/2006 | Motoune et al. |
| 2007/0065547 A1 * | 3/2007 | Coyne et al. ................ 426/326 |
| 2007/0104659 A1 | 5/2007 | Yasuda et al. |
| 2007/0292361 A1 * | 12/2007 | Virgallito et al. ............. 424/49 |

FOREIGN PATENT DOCUMENTS

| EP | 0442671 | 8/1991 |
| EP | 1184029 | 3/2002 |
| EP | 1216091 | 3/2004 |
| EP | 1410794 | 4/2004 |
| EP | 1164849 | 5/2005 |
| EP | 1342471 | 6/2005 |
| EP | 1637188 | 3/2006 |
| GB | 1383281 | 2/1974 |
| JP | S55-102436 | 8/1980 |
| JP | S61-254245 | 11/1986 |
| JP | H01-231934 | 9/1989 |
| JP | 2002-028473 | 1/2002 |
| JP | 2004-525190 | 8/2004 |
| RU | 2098121 | 12/1997 |
| WO | WO 99/17871 | 4/1999 |
| WO | WO 01/01938 | 1/2001 |
| WO | WO 01/07000 | 2/2001 |
| WO | WO 2004/024126 | 3/2004 |
| WO | WO 2005/055967 | 6/2005 |
| WO | WO 2006/065513 | 6/2006 |
| WO | WO 2007026307 A2 * | 3/2007 |

OTHER PUBLICATIONS

Medilexicon [retrieved on Nov. 21, 2012]. Retrieved from the Internet: <URL: http://www.medilexicon.com/medicaldictionary.php?t=18510>.*
American Dental Association [retrieved on Nov. 21, 2012]. Retrieved from the internet: <URL: http://www.ada.org/1322.aspx>.*
Sloan et al (1976). "Prediction of water activity lowering ability of food humectants at high aw" Journal of Food Science., 41: 532-535.*
Decagon Devices [retrieved on Nov. 21, 2012]. Retrieved from the Internet: <URL: http://www.aqualab.com/assets/Uploads/AwDefinition.pdf>.*
PubChem—"Glycerol" [retrieved Sep. 11, 2013]. Retrieved from the internet: <URL: http://pubchem.ncbi.nlm.nih.gov/summary/summary.cgi?cid=753>.*
International Search Report and Written Opinion in International Application No. PCT/US08/82954 mailed Jul. 16, 2009.
Labuza, 1971, "Analysis of Storage Stability of Intermediate Moisture Foods," NASA Final Report, Contract NAS 9-10658, Houston, Texas. pp. 2-3, 12-13, 18-33, 81-84.
Glycerine:an overview, 1990, The Soap and Detergent Association, p. 7.
Personal Care Products Council, "Humectants," 2008, wINCI International Cosmetic Ingredient Dictionary & Handbook, http://webdictionary.personalcarecouncil.org/jsp/ingredinfodropresult-page.jsp?prefe.

* cited by examiner

*Primary Examiner* — Brian-Yong Kwon
*Assistant Examiner* — Doan Phan

(57) ABSTRACT

A capsule slurry including at least one coacervated capsule and at least 10 wt % humectant is disclosed. The humectant may be sorbitol, glycerin, polyethylene glycol, propylene glycol, xylitol, erythritol and/or betaine.

15 Claims, 2 Drawing Sheets

SHELF STABLE CAPSULES

CROSS-REFERENCE TO RELATED PATENT APPLICATIONS

The present application is a national stage entry under 35 U.S.C. §371 of International Patent Application No. PCT/US2008/082954, filed Nov. 10, 2008, the entirety of which is hereby incorporated by reference.

BACKGROUND OF THE INVENTION

Capsules made by a complex coacervation process are often supplied in an aqueous slurry. Often, encapsulated materials can diffuse out the capsule shell through the pores of the capsules into the liquid phase due to the concentration gradient. This leakage may result in the loss of the encapsulated materials. In various applications, such as dentifrice compositions, it may be desirable to reduce the rate of leakage of the capsule contents and increase the capsule stability.

BRIEF SUMMARY OF THE INVENTION

Figure 1:
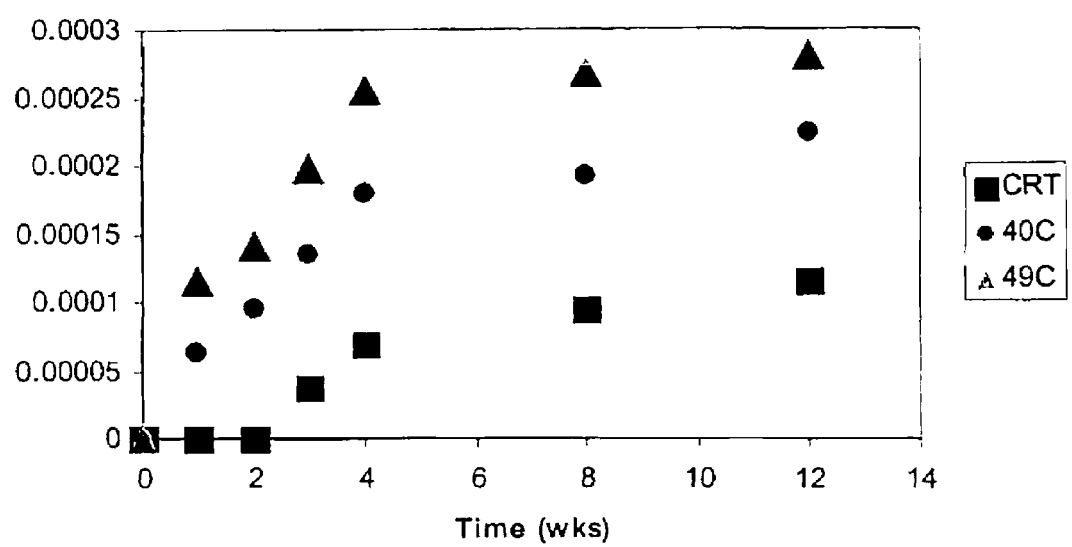
FIG. 1 shows release kinetics of a coacervated flavor capsule.

According to some embodiments, a capsule slurry includes at least one coacervated capsule and at least 10 wt % humectant. It has been found that the humectant reduces the leakage of the capsule contents.

According to some embodiments, a method of reducing leakage of at least one coacervated capsule includes storing coacervated capsules in a capsule slurry which includes at least 10 wt % humectant.

DETAILED DESCRIPTION OF THE INVENTION

As used throughout, ranges are used as a shorthand for describing each and every value that is within the range. Any value within the range can be selected as the terminus of the range.

According to some embodiments, the capsule slurry contains coacervated capsules. In some embodiments, the capsules are core-in-shell capsules.

The capsules may contain any contents suitable for an oral environment. For example, in certain embodiments, the capsules contain active ingredients, flavorants, and/or pigments. The contents may take various forms, such as liquid, solid, powder, and/or gel.

Examples of suitable active ingredients include, but are not limited to, tooth caries preventives, antibiotics, vitamins, enzymes, anti-flammatory agents, and combinations thereof. More specifically, examples thereof include, but are not limited to, sodium fluoride, tin fluoride, sodium monofluorophosphate, vitamin E, vitamin C, dextrinase, mutase, sodium chloride, glycyrrhizinates, glycyrrhetinic acid, azulene, dihydrocholesterol, chlorohexidine, epichlorocholesterol, isopropylmethylphenol, trichlorocarbanilide, triclosan, halocarban, hinokitiol, allantoin, tranexamic acid, propoils, cetylpyridinium chloride, benzethonium chloride, benzalkonium chloride, sodium copper chlorophyllin, and lysozyme chloride.

Examples of suitable flavorants may include, but are not limited to flavoring aldehydes, esters, and alcohols. More specifically, examples thereof include, but are not limited to, spearmint oil, peppermint oil, clove oil, sage oil, eucalyptus oil, laurel oil, cinnamon oil, lemon lime oil, grapefruit oil, menthol, carvone, methyl salicylate, ethyl salicylate, eugenol, camphor oil, ginger, ethyl acetate, diethyl ketone, eucalyptol, pepper, rose, isopropylmethylphenol, maltol, and anethole.

Suitable pigments and dyes may include inorganic and/or organic pigments. More specifically, examples thereof may include, but are not limited to, inorganic pigments such as cobalt blue, cobalt green, yellow iron oxide, titanium oxide, mica, zinc powder, and aluminum powder; lake pigments such as Blue No. 1 and Red No. 2; and other pigments such as copper chlorophyll, .beta.-carotene, and iron complex salts of hinokitiol.

In certain embodiments, the contents of the capsules are blended with vehicles such as fats and oils, waxes, hydrocarbons, higher fatty acids, higher alcohols, esters, essential oils, and silicone oils. Examples of suitable fats and oils may include, but are not limited to, natural fats and oils such as soybean oil, rice bran oil, jojoba oil, avocado oil, almond oil, olive oil, cacao butter, sesame oil, persic oil, castor oil, coconut oil, mink oil, beef tallow, and lard; hydrogenated oils obtained by hydrogenation of these natural fats and oils; and synthetic triglycerides such as myristic glyceride, 2-ethylhexanoic glyceride, tricaprylic glyceride, and tricapric glyceride. Examples of suitable waxes may include, but are not limited to, carnauba wax, whale wax, beeswax, and lanoline. Examples of suitable hydrocarbons may include, but are not limited to, liquid paraffins, vaseline, paraffins, microcrystalline waxes, ceresin, squalane, and pristane. Examples of suitable higher fatty acids may include, but are not limited to, lauric acid, myristic acid, palmitic acid, stearic acid, behenic acid, oleic acid, linoleic acid, linolenic acid, lanolic acid, and isostearic acid. Examples of suitable higher alcohols may include, but are not limited to, lauryl alcohol, cetyl alcohol, stearyl alcohol, oleyl alcohol, lanoline alcohol, cholesterol, and 2-hexyldecanol. Examples of suitable esters may include, but are not limited to, cetyl octanoate, myristyl lactate, cetyl lactate, isopropyl myristate, myristyl myristate, isopropyl palmitate, isopropyl adipate, butyl stearate, and decyl oleate. Examples of the essential oils may include, but are not limited to, mentha oil, jasmine oil, camphor oil, hinoki oil, tohi oil, rue oil, turpentine oil, cinnamon oil, bergamot oil, citrus oil, calamus oil, pine oil, lavender oil, bay oil, clove oil, hiba oil, rose oil, eucalyptus oil, lemon oil, peppermint oil, and sage oil. Examples of the silicone oils include dimethylpolysiloxane.

In some embodiments, the core of the capsule is a liquid. In some embodiments, the core of the capsule is a solid. In certain embodiments, the core of the capsule is a combination of liquid and solid.

In certain embodiments, the capsules are formed by a coacervation process. In some embodiments, the capsules are formed by a complex coacervation process. Coacervation processes known in the art may be used, including, for example, those described in U.S. Pat. No. 6,045,835, the contents of which are incorporated herein by reference. Average particle size for the capsules may be 1 to 3,000 microns, 50 to 2,000 microns, or 500 to 1500 microns. The capsules may have an average wall thickness of 10 to 40 microns, although any desired thickness may be used.

The core-to-wall ratio of the capsules may be any suitable for the desired end product and/or method of processing intended for the end product. It may be, for example, of 10 to 1, 12 to 1, 16 to 1, and/or 20 to 1; however, any ratio may be suitable if such ratio provides sufficient stability of the capsule during manufacture and allows for sufficient breakage during use.

Following the coacervation process, the capsules may be washed to remove residual material and subsequently incorporated into a representative slurry formulation containing other ingredients, such as, for example, a humectant.

According to some embodiments, capsules are stored while in a slurry with additional constituents. In some embodiments, the slurry is aqueous. In certain embodiments, the slurry contains 1 to 80 wt % water. In some embodiments, the slurry contains 1 to 70 wt % water. In some embodiments, the slurry contains 1 to 50 wt % water. In some embodiments, the slurry contains 1 to 40 wt % water. In some embodiments, the slurry contains 1 to 30 wt % water. In some embodiments, the slurry contains 1 to 20 wt % water. In some embodiments, the slurry contains 1 to 15 wt % water. In other embodiments, the slurry contains no water.

In some embodiments, the slurry contains at least one humectant. Examples of suitable humectants may include, but are not limited to, sorbitol, glycerin, polyethylene glycol, propylene glycol, erythitrol, and betaine. In some embodiments, the slurry contains at least 15 wt % humectant. In some embodiments, the slurry contains at least 20 wt % humectant. In some embodiments, the slurry contains at least 40 wt % humectant. In some embodiments, the slurry contains at least 65 wt % humectant. In some embodiments, the slurry contains at least 80 wt % humectant.

According to some embodiments, the slurry contains capsules as described above. In some embodiments, the slurry may contain 5 to 65 wt % capsules. In some embodiments, the slurry may contain 20 to 50 wt % capsules. In some embodiments, the slurry may contain 30 to 35 wt % capsules.

According to some embodiments, the slurry includes thickeners. The slurry may contain any suitable thickener. Examples of suitable thickeners may include, but are not limited to, xanthan gum, sodium salts of carboxymethyl cellulose, sodium polyacrylates, hydroxyethyl cellulose, thickened silica, carrageenan, sodium alginate, montmorillonite, gum guar, and pectin. In some embodiments, the slurry contains up to 10 wt % thickener. In certain embodiments, the slurry contains up to 5 wt % thickener. In some embodiments, the slurry contains up to 1 wt % thickener.

In certain embodiments, the slurry includes preservatives. The slurry may contain any suitable preservative. Examples of suitable preservatives may include, but are not limited to, potassium sorbate, benzoic acid, sodium benzoate, parabens, parahydroxybenzoic esters, and the like. In some embodiments, the slurry contains any suitable amount of preservatives. In some embodiments, the slurry contains up to 10 wt % preservatives. In other embodiments, the slurry contains up to 5 wt % preservatives. In certain embodiments, the slurry contains up to 1 wt % preservatives.

According to some embodiments, the capsule slurry is incorporated in a dentifrice composition. The dentifrice composition may take any desired form, including toothpastes, tooth powders, prophylaxis pastes, gels, rinses, lozenges, gums and the like.

In some embodiments, the dentifrice composition includes up to 30 wt % of the capsule slurry. In certain embodiments, the dentifrice composition includes up to 15 wt % of the capsule slurry. In other embodiments, the dentifrice composition includes up to 5 wt % of the capsule slurry. In some embodiments, the dentifrice composition includes up to 1 wt % of the capsule slurry.

In some embodiments, the dentifrice composition includes materials such as fluoride ion sources, anti-calculus agents, buffers, abrasive materials, peroxide sources, alkali metal bicarbonate salts, thickening materials, humectants, water, surfactants, flavor system, sweetening agents, coloring agents, and mixtures thereof. In certain embodiments, the dentifrice composition includes the usual components of toothpastes, tooth powders, prophylaxis pastes, gels, rinses, lozenges, gums and the like.

In some embodiments, a dentifrice composition includes water. In some embodiments, the dentifrice composition includes water in an amount of 1 to 95 wt %. In some embodiments, the dentifrice composition includes water in an amount of 1 to 50 wt %. In some embodiments, the dentifrice composition includes water in an amount of 10 to 40 wt % water.

The dentifrice composition may also include a humectant. In some embodiments, the humectant includes glycerin, sorbitol, erythritol, betaine or an alkylene glycol such as polyethylene glycol or propylene glycol. In some embodiments, the humectant is present in an amount of 15 to 95 wt % of the dentifrice composition. In other embodiments, the humectant is present in an amount of 45 to 85 wt %.

The dentifrice composition may include an inorganic or a natural or synthetic thickening or gelling agent. In some embodiments, the thickening or gelling agent is present in an amount of up to 10 wt %. Other levels that may be suitable include 0.25% to 5%, 0.5% to 4%, and/or 1% to 3%, by weight of the total composition. In some embodiments, a suitable amount of thickening agent is included in the dentifrice composition to suspend capsules, or abrasive granules or beads. In some embodiments, a suitable amount of thickening agent is included in the dentifrice composition to form an extrudable, shape-retaining product which can be squeezed from a tube onto a toothbrush and will not fall between the bristles of the brush but rather, will substantially maintain its shape thereon. Suitable thickening or gelling agents for a dentifrice composition may include inorganic thickening silicas available from Huber Corporation, Edison, N.J. under the trade name designation of Zeodent 165, Irish moss, carrageen, gum tragacant, polyvinylpyrrolidone, xanthan gum, sodium salts of carboxymethyl cellulose, sodium polyacrylates, hydroxyethyl cellulose, thickened silica, montmorillonite, sodium alginate, gum guar, silicates, alkali metal silicates, such as laponite, and pectin.

In some embodiments, the dentifrice composition includes at least one surfactant. Suitable surfactants may include, but are not limited to, water-soluble salts of higher fatty acid monoglyceride monosulfates, such as the sodium salt of the monosulfated monoglyceride of hydrogenated coconut oil fatty acids, cocamidopropyl betaine, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of suitable amides may include N-lauroyl sarcosine, and the sodium, potassium, and ethanolamine salts of N-lauroyl, N-myristoyl, or N-palmitoyl sarcosine.

In some embodiments, the dentifrice composition contains up to 5.0 wt % surfactants. In other embodiments, the dentifrice composition contains 0.5 to 2.5 wt % surfactants. In some embodiments, the dentifrice composition contains 1 wt % surfactants.

The dentifrice composition may also contain a binder agent. Examples of suitable binder agents may include, but are not limited to, marine colloids, carboxyvinyl polymers, carrageenans, starches, water-soluble cellulose ethers such as hydroxyethylcellulose, carboxymethylcellulose (carmellose), hydroxypropyl methyl cellulose and salts thereof (e.g., carmellose sodium), natural gums such as karaya, xanthan, gum arabic and tragacanth, chitosan, colloidal magnesium aluminum silicate, and colloidal silica. In some embodiments, the binding agents are present in an amount of 0.1 to 1.5 percent by weight.

The dentifrice compositions may also include a flavorant or a mixture of flavorants, including natural or synthetic flavorants, such as flavoring oils, flavoring aldehydes, esters, alcohols, similar materials, and combinations thereof. Examples of suitable flavorants may include vanillin, spearmint oil, cinnamon oil, oil of wintergreen (methylsalicylate), peppermint oil, clove oil, anise oil, eucalyptus oil, citrus oils, fruit oils and essences. In some embodiments, the dentifrice composition includes flavorants such as limonene, menthone, carvone, menthol, anethole, eucalyptus oil, eucalyptol, eugenol, cassia, oxanone, alpha-irisone, propenyl guaiethol, thymol, linalool, benzaldehyde, cinnamaldehyde, N-ethyl-p-menthan-3-carboxamine, N-2,3-trimethyl-2-isopropylbutanamide, 3,1-menthoxypropane-1,2-diol, cinnamaldehyde glycerol acetal (CGA), methone glycerol acetal (MGA) and cineole.

In some embodiments, the dentifrice composition may also include an abrasive. An abrasive may act as a mechanical and physical means of exfoliation and increased desquamation of the oral mucosa. In some embodiments, the abrasive is distributed throughout an orally acceptable vehicle.

In some embodiments, the dentifrice composition includes silica abrasives. Examples of suitable abrasives include, but are not limited to, silica abrasives such as precipitated silicas, sodium metaphosphate, potassium metaphosphate, tricalcium phosphate, dihydrated dicalcium phosphate, aluminum silicate, calcined alumina, bentonite or other siliceous materials, particulate thermosetting resins, such as melamine, phenolic, and urea-formaldehydes, and cross-linked polyepoxides and polyesters.

An abrasive may be present in any suitable amount. In some embodiments, such abrasives are present in an amount of 1 to 50 percent by weight. In other embodiments, such abrasives are present in an amount of 10 to 40 percent by weight. In other embodiments, such abrasives are present in an amount of 18 to 20 percent by weight.

Other additives may be included in the dentifrice composition for reasons of manufacturing, stability, aesthetics, therapeutic effect, consumer appeal, etc. Exemplary additive include all other conventional dentifrice additives, viscosity modifiers, diluents, foam modulators, saliva stimulating agents, desensitizing agents, whitening agents, enzymes, pH modifying agents, mouth-feel agents, sweeteners, colorants, opacifiers, and breath freshening agents.

According to some embodiments of the present invention, a capsule slurry includes coacervated capsules and at least 10 wt % humectant. In some embodiments, storing coacervated capsules in a capsule slurry that includes at least 10 wt % humectant reduces the leakage of the contents of the coacervated capsules.

Figure 2:
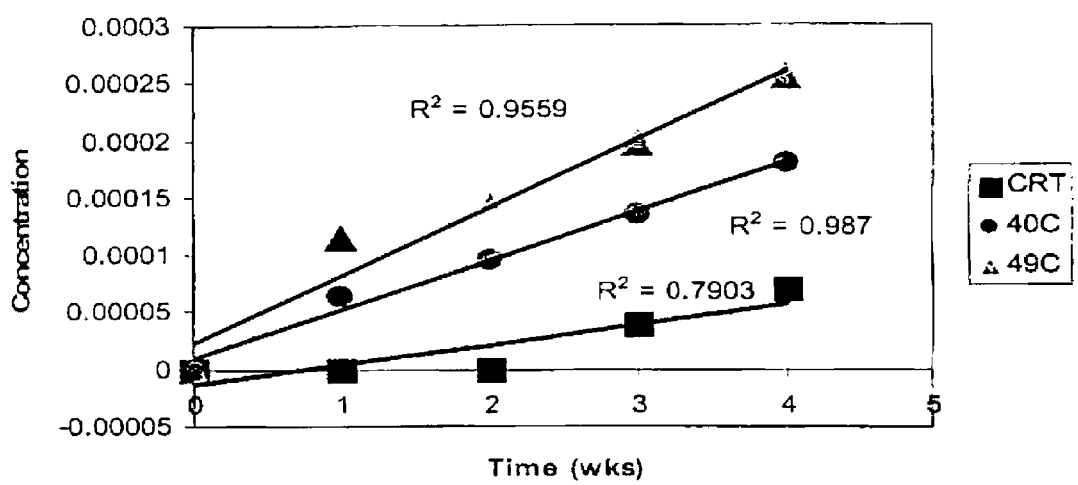
FIG. 2 shows initial phase release kinetics of a coacervated flavor capsule.

Referring to FIG. 1, in some embodiments the leakage of the contents of a flavor capsule made by a complex coacervation process demonstrates two-phase kinetics. As shown in FIG. 1, in certain embodiments the leakage occurs with an initial fast phase with a half life in the weeks/months time scale followed by a slow equilibrium phase. Referring to FIG. 2, a detailed analysis of the fast phase kinetics reveals that in certain embodiments the leakage rate follows zero-order kinetics. As shown in FIG. 2, in some embodiments the flavor component leaks at a constant rate; the rate is the slope of the linear fit of the leakage data.

According to some embodiments, capsules are stored in a slurry to reduce leakage of the contents of the capsule. In some embodiments, the capsules are stored in a slurry that includes at least 15 wt % humectant. In some embodiments, the capsules are stored in a slurry that includes at least 20 wt % humectant. In some embodiments, the capsules are stored in a slurry that includes at least 40 wt % humectant. In some embodiments, the capsules are stored in a slurry that includes at least 65 wt % humectant. In some embodiments, the capsules are stored in a slurry that includes at least 80 wt % humectant. In certain embodiments, the capsules are coacervated.

According to some embodiments, the leakage rate of the contents of the capsules contained in the slurry is less than 4e-10 M/sec at room temperature. In some embodiments, the leakage rate of the contents of the capsules contained in the slurry is less than 4e-11 M/sec at room temperature. In some embodiments, the leakage rate of the contents of the capsules contained in the slurry is less than 1.5e-11 M/sec at room temperature.

According to some embodiments, the leakage rate of the contents of the capsules contained in the slurry is less than 1e-9 M/sec at 40° C. In some embodiments, the leakage rate of the contents of the capsules contained in the slurry is less than 1e-10 M/sec at 40° C. In certain embodiments, the leakage rate of the contents of the capsules contained in the slurry is less than 8e-11 M/sec at 40° C.

According to some embodiments, the leakage rate of the contents of the capsules contained in the slurry is less than 1.5e-9 M/sec at 49° C. In certain embodiments, the leakage rate of the contents of the capsules contained in the slurry is less than 1.5e-10 M/sec at 49° C. In some embodiments, the leakage rate of the contents of the capsules contained in the slurry is less than 1e-10 M/sec at 49° C.

Water activity of the slurry is defined as the vapor pressure of water above a slurry sample divided by the vapor pressure of pure water at the same temperature and pressure. It is measured using a dew point hygrometer. In some embodiments, the slurry has a water activity at 23° C. of less than 0.97. In certain embodiments, the slurry has a water activity at 23° C. of less than 0.95. In some embodiments, the slurry has a water activity at 23° C. of less than 0.94. In some embodiments, the slurry has a water activity at 23° C. of less than 0.90. In some embodiments, the slurry has a water activity at 23° C. of less than 0.85.

According to some embodiments, the amount of humectant in the slurry is related to the leakage rate of the contents of the capsules contained in the slurry. In some embodiments, the leakage rate of the contents of the capsules is inversely related to the amount of humectant in the slurry. In certain embodiments, a higher concentration of humectant in the slurry results in a lower leakage rate of the contents of the capsules contained in the slurry.

According to some embodiments, the amount of humectant in the slurry is related to the water activity of the slurry. In certain embodiments, the water activity of the slurry is inversely related to the humectant concentration in the slurry. In some embodiments, a higher concentration of humectant in the slurry results in a lower water activity of the slurry.

In some embodiments, the water activity of the slurry is related to the leakage rate of the contents of the capsules contained in the slurry. In certain embodiments, the water activity of the slurry has a direct relationship with the leakage rate of the contents of the capsules contained in the slurry. In some embodiments, a lower water activity of the slurry results in a lower leakage rate of the contents of the capsules contained in the slurry.

According to some embodiments, capsules are contained in a dentifrice composition to reduce leakage of the contents of the capsule. In some embodiments, capsules are contained in a dentifrice composition including humectant in an amount of 15 to 95 wt % of the dentifrice composition. In other embodiments, capsules are contained in a dentifrice composition including humectant in an amount of 45 to 85 wt %. In certain embodiments, the capsules are coacervated.

According to some embodiments, the leakage rate of the contents of the capsules contained in the dentifrice composition is less than 5e-9 M/sec at room temperature. In some embodiments, the leakage rate of the contents of the capsules contained in the dentifrice composition is less than 1e-9 M/sec at room temperature. In some embodiments, the leakage rate of the contents of the capsules contained in the dentifrice composition is less than 3e-10 M/sec at room temperature.

According to some embodiments, the leakage rate of the contents of the capsules contained in the dentifrice composition is less than 7e-9 M/sec at 40° C. In some embodiments, the leakage rate of the contents of the capsules contained in the dentifrice composition is less than 4e-9 M/sec at 40° C. In certain embodiments, the leakage rate of the contents of the capsules contained in the dentifrice composition is less than 2e-9 M/sec at 40° C.

According to some embodiments, the leakage rate of the contents of the capsules contained in the dentifrice composition is less than 8e-9 M/sec at 49° C. In certain embodiments, the leakage rate of the contents of the capsules contained in the dentifrice composition is less than 6e-9 M/sec at 49° C. In some embodiments, the leakage rate of the contents of the capsules contained in the dentifrice composition is less than 5e-9 M/sec at 49° C.

In some embodiments, the dentifrice composition has a water activity at 23° C. of less than 0.95. In certain embodiments, the dentifrice composition has a water activity at 23° C. of less than 0.90. In some embodiments, the dentifrice composition has a water activity at 23° C. of less than 0.80. In some embodiments, the dentifrice composition has a water activity at 23° C. of less than 0.70. In some embodiments, the dentifrice composition has a water activity at 23° C. of less than 0.60.

According to some embodiments, the amount of humectant in the dentifrice composition is related to the leakage rate of the contents of the capsules contained in the dentifrice composition. In some embodiments, the leakage rate of the contents of the capsules is inversely related to the amount of humectant in the dentifrice composition. In certain embodiments, a higher concentration of humectant in the dentifrice composition results in a lower leakage rate of the contents of the capsules contained in the dentifrice composition.

According to some embodiments, the amount of humectant in the dentifrice composition is related to the water activity of the dentifrice composition. In certain embodiments, the water activity of the dentifrice composition is inversely related to the humectant concentration in the dentifrice composition. In some embodiments, a higher concentration of humectant in the dentifrice composition results in a lower water activity of the dentifrice composition.

In some embodiments, the water activity of the dentifrice composition is related to the leakage rate of the contents of the capsules contained in the dentifrice composition. In certain embodiments, the water activity of the dentifrice composition has a direct relationship with the leakage rate of the contents of the capsules contained in the dentifrice composition. In some embodiments, a lower water activity of the dentifrice composition results in a lower leakage rate of the contents of the capsules contained in the dentifrice composition.

EXAMPLES

The following examples further describe and demonstrate embodiments within the scope of the present invention. These examples are given solely for the purpose of illustration and are not to be construed as a limitation of the present invention as many variations thereof are possible without departing from the spirit and scope.

Example 1

Capsule Slurry Formulations

Capsule slurry formulations with coacervated capsules containing flavorants were prepared with no sorbitol, 20 wt % sorbitol, and 40 wt % sorbitol, A, B and C respectively. Table 1 lists the contents in weight percent and the water activity ($A_w$) at 23° C. for each capsule slurry formulation.

TABLE 1

Water Activity for Capsule Slurry Formulations

| Formula (wt %) | A | B | C |
|---|---|---|---|
| Water | 66.2 | 46.2 | 26.2 |
| Sorbitol (active) | — | 20 | 40 |
| Flavor capsule | 33 | 33 | 33 |
| Xanthan Gum | 0.2 | 0.2 | 0.2 |
| Potassium Sorbate | 0.5 | 0.5 | 0.5 |
| $A_w$ @ 23° C. | 0.97 | 0.91 | 0.84 |

The data shows that a higher concentration of Sorbitol corresponds with a lower leakage rate at each temperature.

Table 2 lists the leakage rates (M/sec) of the flavor contents of the coacervated capsules contained in the slurries at various temperatures.

TABLE 2

Leakage Rates of Flavor Contents of Capsules in Slurry (M/sec)

| Temperature | A | B | C |
|---|---|---|---|
| Room Temp | $3.4 \times 10^{-9}$ | $4.0 \times 10^{-11}$ | $1.4 \times 10^{-11}$ |
| 40° C. | $4.5 \times 10^{-9}$ | $9.8 \times 10^{-11}$ | $7.9 \times 10^{-11}$ |
| 49° C. | $7.4 \times 10^{-9}$ | $1.4 \times 10^{-10}$ | $9.7 \times 10^{-11}$ |

The data demonstrate that a higher concentration of sorbitol in a capsule slurry corresponds with a lower water activity at 23° C. of the capsule slurry.

Example 2

Dentifrice Compositions Containing Capsules and Leakage Rates

Dentifrice compositions containing flavor-filled coacervated capsules were prepared with various amounts of humectant and water. The flavor-filled capsules have a an outer coating of 93% medium chain triglycerides and 7% protein surrounding the flavor liquid that comprises between 20 and 30% by weight of the capsule. Table 3 lists the contents in weight percent and the water activity ($A_w$) at 23° C. for each dentifrice composition.

TABLE 3

Dentifrice Liquid Phase Compositions

| Formula (wt %) | A | B | C |
|---|---|---|---|
| Water | 40 | 25 | 10 |
| Glycerin | 10 | 25 | 40 |
| Dental Silica - Abrasive | 20 | 20 | 20 |
| Dental Silica - Thickener | 4.2 | 4.2 | 4.2 |
| Sorbitol | 14.6 | 14.6 | 14.6 |
| PEG 600 | 3 | 3 | 3 |
| Pluronic F127 | 1.5 | 1.5 | 1.5 |
| CAP Betaine | 1 | 1 | 1 |
| SLS | 1 | 1 | 1 |
| CMC Gum | 1.5 | 1.5 | 1.5 |
| Mint Flavor | 0.7 | 0.7 | 0.7 |
| Na Saccharin | 0.5 | 0.5 | 0.5 |
| Tetrasoium Pyrophosphate | 0.5 | 0.5 | 0.5 |
| Sodium Fluoride | 0.3 | 0.3 | 0.3 |
| Parabens | 0.1 | 0.1 | 0.1 |
| Flavor Capsule | 1 | 1 | 1 |
| $A_w$ @ 23° C. | 0.88 | 0.78 | 0.59 |

The data show that a higher concentration of humectant in a dentifrice composition corresponds with a lower water activity at 23° C. of the dentifrice composition.

Dentifrice compositions with coacervated capsules containing flavorants were prepared with various amounts of humectant and water listed in Table 3 as A, B and C. Table 4 lists the leakage rate (M/sec) of the flavor contents of the coacervated capsules contained in the dentifrice composition at various temperatures.

TABLE 4

Leakage Rates of Flavor Contents of Capsules in Dentifrice Composition (M/sec)

| Temperature | A | B | C |
|---|---|---|---|
| Room Temperature | $4 \times 10^{-9}$ | $9 \times 10^{-10}$ | $2 \times 10^{-10}$ |
| 40° C. | $6 \times 10^{-9}$ | $3 \times 10^{-9}$ | $1 \times 10^{-9}$ |
| 49° C. | $7 \times 10^{-9}$ | $5 \times 10^{-9}$ | $4 \times 10^{-9}$ |

The data shows that a higher concentration of glycerin corresponds with a lower leakage rate at each temperature.

We claim:

1. A capsule slurry comprising:
    at least one coacervated capsule, the at least one coacervated capsule having a wall formed from triglycerides and protein; and
    at least 40 wt % humectant;
    wherein the at least one coacervated capsule contains a flavorant and the leakage rate of the flavorant from the at least one coacervated capsule contained in the capsule slurry is less than $9.7 \times 10^{-11}$ M/sec at room temperature.

2. The capsule slurry of claim 1, wherein the humectant is sorbitol.

3. The capsule slurry of claim 1, wherein the humectant is glycerin.

4. The capsule slurry of claim 1, wherein the capsule slurry comprises at least 65 wt % humectant.

5. The capsule slurry of claim 4, wherein the capsule slurry comprises at least 80 wt % humectant.

6. The capsule slurry of claim 1, wherein the capsule slurry has a water activity of less than 0.94 at 23° C.

7. A dentifrice composition including the capsule slurry of claim 1, wherein the at least one coacervated capsule contains a flavorant and the leakage rate of the flavorant from the at least one coacervated capsule contained in the dentifrice composition is less than $4 \times 10^{-9}$ M/sec at room temperature.

8. The dentifrice composition of claim 7, wherein the capsule slurry is present in an amount of 0.1 to 10 wt %.

9. The dentifrice composition of claim 7, wherein the capsule slurry is present in an amount of 0.5 to 5 wt %.

10. The dentifrice composition of claim 1, wherein the flavorant is selected from the group consisting of spearmint oil, peppermint oil, clove oil, sage oil, eucalyptus oil, laurel oil, cinnamon oil, lemon lime oil, grapefruit oil, menthol, carvone, methyl salicylate, ethyl salicylate, eugenol, camphor oil, ginger, ethyl acetate, diethyl ketone, eucalyptol, pepper, rose, isopropylmethylphenol, maltol, and anethole.

11. A method of reducing leakage of coacervated capsules comprising storing at least one coacervated capsule in a capsule slurry of claim 1.

12. The method of claim 11, wherein the humectant is sorbitol.

13. The method of claim 11, wherein the humectant is glycerin.

14. The dentifrice composition of claim 7, wherein the flavorant is selected from the group consisting of spearmint oil, peppermint oil, clove oil, sage oil, eucalyptus oil, laurel oil, cinnamon oil, lemon lime oil, grapefruit oil, menthol, carvone, methyl salicylate, ethyl salicylate, eugenol, camphor oil, ginger, ethyl acetate, diethyl ketone, eucalyptol, pepper, rose, isopropylmethylphenol, maltol, and anethole.

15. The capsule slurry of claim 1, wherein
    the slurry contains 10 to 30 wt. % water; and
    the leakage rate of the contents of the capsules is less than $7.9 \times 10^{-11}$ M/sec. at room temperature.

* * * * *